(12) United States Patent
Paul

(10) Patent No.: US 6,478,797 B1
(45) Date of Patent: Nov. 12, 2002

(54) SPINAL FIXATION DEVICE

(76) Inventor: Kamaljit S. Paul, 3220 Old Orchard La., Oshkosh, WI (US) 54901

( * ) Notice: Subject to any disclaimer, the term of this patent is extended or adjusted under 35 U.S.C. 154(b) by 0 days.

(21) Appl. No.: 09/858,417

(22) Filed: May 16, 2001

(51) Int. Cl.[7] .............................................. A61B 17/56
(52) U.S. Cl. .............................. 606/61; 606/72; 606/73
(58) Field of Search ............................. 606/61, 70, 71, 606/72, 73, 69, 68; 623/17.16

(56) References Cited

U.S. PATENT DOCUMENTS

| | | | |
|---|---|---|---|
| 5,261,912 A | * | 11/1993 | Frigg ............................ 606/61 |
| 5,346,493 A | * | 9/1994 | Stahurski et al. .............. 606/61 |
| 5,360,431 A | * | 11/1994 | Puno et al. |
| 5,683,390 A | * | 11/1997 | Metz-Stavenhagen et al. ........ 606/61 |
| 5,713,898 A | * | 2/1998 | Stucker et al. ................. 606/70 |
| 6,251,112 B1 | * | 6/2001 | Jackson ........................ 606/61 |
| 6,302,888 B1 | * | 10/2001 | Mellinger et al. ............ 606/73 |

* cited by examiner

Primary Examiner—Pedro Philogene
(74) Attorney, Agent, or Firm—Wilhelm Law Service; Thomas D. Wilhelm (57) ABSTRACT

A spinal fixation device comprises attachment component, seat, seat fastener, and saddle. The attachment component secures the fixation device to bone. The seat comprises an inner seat surface, an outer seat surface, a brace canal along the inner seat surface, and a channel or lip at the outer seat surface. The seat fastener has a cooperating lip or channel at an inner surface. The saddle is between a brace member and the seat fastener. The channel and cooperating lip of the seat and seat fastener cooperatively engage the seat to the seat fastener, whereby tightening the lip and channel to each other compresses the saddle between the seat and seat fastener, thereby to lock the brace member to the seat. The cooperative engagement between lip and channel is preferably achieved by rotating the seat fastener approximately 90 degrees with respect to an axis which extends perpendicular to the brace fastener.

26 Claims, 5 Drawing Sheets

SPINAL FIXATION DEVICE

BACKGROUND

Spinal fixation devices are used to stabilize surgically fused vertebrae. Conventional devices consist of an assembly generally made up of titanium bone screws, reinforcing rods, and other components. A certain level of complexity exists in installing spinal fixation devices in that the implementor has to twist as many as two dozen threaded fasteners onto respective bone screws and/or bone hooks.

Threadings, in the context of spinal fixation devices, provide a variety of fundamental problems during installation. Since spinal devices generally need to be assembled through an incision, it can be difficult to catch the first thread amongst the surrounding soft tissue, blood, and other fluids. Additionally, some screws installed in an incision environment can too easily suffer from cross-threading.

As another shortcoming of conventional spinal fixation devices, threadings on screws and nuts allow for inconsistent tightening during installation. The installation of apparatuses which include threadings allow for different implementors to apply a wide range of torque levels, some in excess of the desired amount, thus increasing the chance of surgical slips during installation, as well as equipment failure.

Further, it is well known that prolonging the time of surgery both increases the patient's risk of infection as well as complications associated with anesthesia. The use of threaded screws and nuts can consume significant amounts of surgical time that ideally would be avoided.

Additionally, threaded fasteners are problematic in that such traditional set screws can work their way loose when confronted with continuous micro-motion of the spine.

As yet another shortcoming of some conventional spinal fixation devices, fasteners are fastened to the interior surface of respective channeled hooks and/or screws to immobilize rods positioned in such channels. While using a fastener that fits into the screw and/or hook may be desirable for the sake of saving space, such a design does allow for the possibility of channels widening over time until the device fails.

A need exists for a spinal fixation device, and corresponding fastener of such device, that can be assembled in an improved amount of time, with less chance of inaccuracies, and with greater reliability than conventional methods.

It is therefore an object of this invention to provide a spinal fixation device, for use in the incision environment, which lacks complex assembly steps.

It is another object of this invention to provide a spinal fixation device in which substantially uniform torque is required to assemble such spinal fixation device.

It is yet another object of this invention to provide a spinal fixation device which enables an installer to affix the device to a recipient with greater time-efficiency than conventional methods.

It is still another object of this invention to provide a spinal fixation device which does not loosen due to mechanical failure of the device or normal micro-motions of the vertebrae.

SUMMARY

In a first family of embodiments, the invention comprehends a spinal fixation device for use with an elongate brace member. The spinal fixation device comprises an attachment component, a seat, a seat fastener, and a saddle. The attachment component functions to secure the spinal fixation device to a desired bone structure. The seat comprises an inner seat surface and an outer seat surface. The seat has a brace canal along the inner seat surface for positioning of the brace member, and the outer seat surface has a locking channel. The seat fastener has a top, a bottom, an outer side surface, and an inner side surface; the inner side surface includes a lip. The saddle is disposed between the brace member and the seat fastener. The locking channel of the seat is designed and configured to form a cooperative engagement with the lip of the seat fastener, thereby enabling the lip of the seat fastener to lockingly engage the locking channel of the seat. The brace member is compressively loaded into a cooperation with the seat and the saddle by compression resulting from tightening of the seat fastener to the seat so as to lock the relative position between the seat and the bone attachment component.

In preferred embodiments, the saddle is adapted to bear upon the elongate brace member, upon tightening of the seat fastener, thereby to compress the elongate brace member into a secure engagement with the brace canal of the seat.

In most embodiments, the attachment component is a threaded screw portion, a lamina hook, or a pedicle hook.

Preferably, the cooperative engagement between the lip of the seat fastener and the locking channel of the seat is a high friction interface.

In some embodiments, the lip of the seat fastener further comprises a lock-notch, and the locking channel of the seat further comprises a complimentary lock-groove, whereby, upon sufficient tightening, the lock-notch interfaces with the lock-groove, thereby further securing the cooperative engagement between the lip of the seat fastener and the locking channel of the seat.

In other embodiments, the lip of the seat fastener further comprises a lock-groove, and the locking channel of the seat further comprises a complimentary lock-notch, whereby, upon sufficient tightening, the lock-notch interfaces with the lock-groove, thereby further securing the cooperative engagement between the lip of the seat fastener and the locking channel of the seat.

In preferred embodiments, the cooperative engagement between the lip of the seat fastener and the locking channel of the seat is achieved by turning the seat fastener approximately 90 degrees.

The spinal fixation device is generally one or both anodized and made of titanium.

In preferred embodiments, the lip tapers about 0.04 inch to about 0.05 inch over a 180 degree arc.

In some embodiments, the seat and the seat fastener both have visual orientation indicators which come into alignment upon tightening the seat fastener to the seat by cooperatively engaging the lip of the seat fastener and the locking channel of the seat, and turning the seat fastener approximately 90 degrees.

In a second family of embodiments, the invention comprehends a spinal fixation device for use with an elongate brace member. In such embodiments, the outer seat surface of the seat has a lip, and the inner side surface of the seat fastener includes a locking channel. Accordingly, the locking channel of the seat fastener is designed and configured to form a cooperative engagement with the lip of the seat, thereby enabling the lip of the seat to lockingly engage the locking channel of the seat fastener. The brace member is compressively loaded into a cooperation with the seat and the saddle by compression resulting from tightening of the seat fastener to the seat so as to lock the relative position between the seat and the bone attachment component.

In preferred embodiments, the cooperative engagement between the lip of the seat and the locking channel of the seat fastener is a high friction interface.

In some embodiments, the lip of the seat further comprises a lock-notch, and the locking channel of the seat fastener further comprises a complimentary lock-groove, whereby, upon sufficient tightening, the lock-notch interfaces with the lock-groove, thereby further securing the cooperative engagement between the lip of the seat and the locking channel of the seat fastener.

In other embodiments, the lip of the seat further comprises a lock-groove, and the locking channel of the seat fastener further comprises a complimentary lock-notch, whereby, upon sufficient tightening, the lock-notch interfaces with the lock-groove, thereby further securing the cooperative engagement between the lip of the seat and the locking channel of the seat fastener.

Preferably, the cooperative engagement between the lip of the seat and the locking channel of the seat fastener is achieved by turning the seat fastener approximately 90 degrees.

In some embodiments, the seat and the seat fastener both have visual orientation indicators which align upon tightening the seat fastener to the seat by cooperatively engaging the lip of the seat and the locking channel of the seat fastener, and turning the seat fastener approximately 90 degrees.

The invention is not limited in its application to the details of construction or the arrangement of the components set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1:
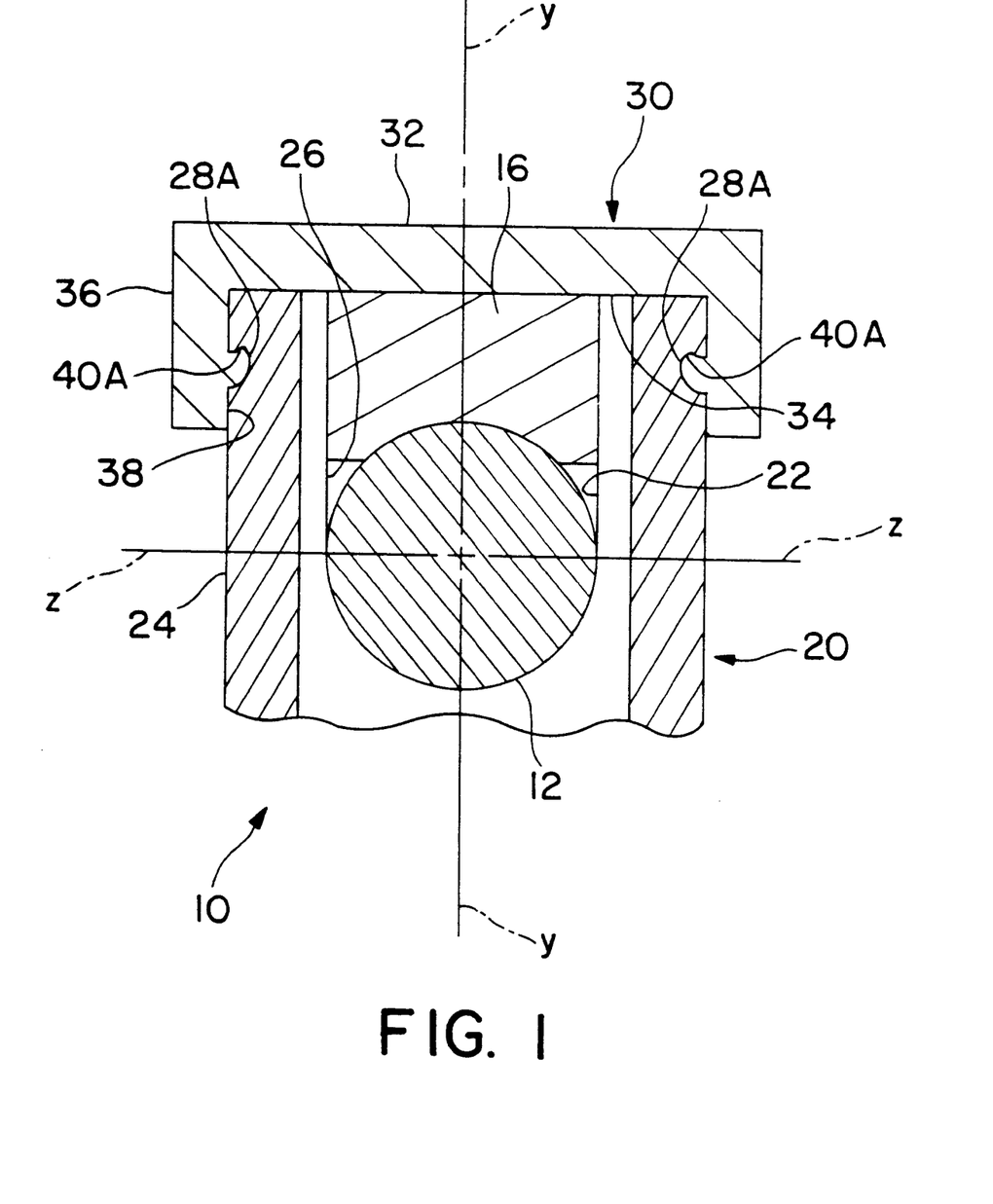
FIG. 1 is an enlarged cross-section of a first embodiment of the device relationally illustrating a seat, saddle, brace member, and seat fastener.
Figure 2:
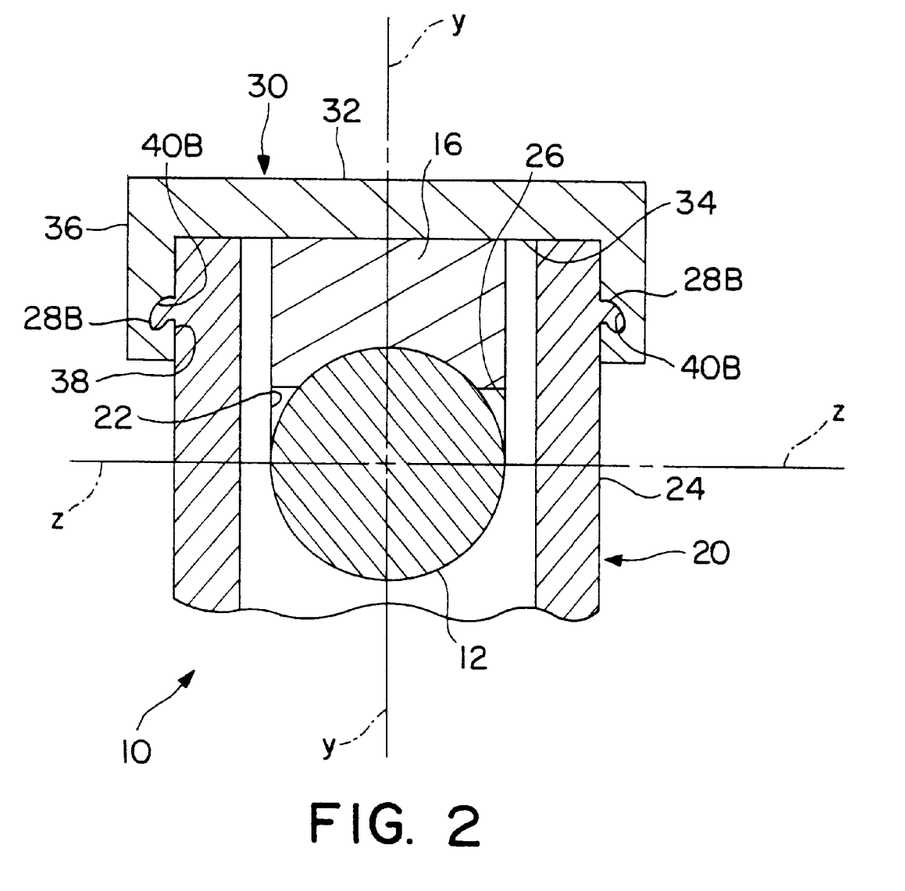
FIG. 2 is an enlarged cross-section of a second embodiment of the device relationally illustrating a seat, saddle, brace member, and accompanying seat fastener.

Referring to FIGS. 1 and 2, the present invention relates to a fastening system for spinal fixation devices, and spinal fixation devices 10 using such fastening system, which is generally used in conjunction with an elongate brace member 12, for fixation and/or manipulation of the spine. The spinal fixation device comprises an attachment component 14 (illustrated in FIGS. 3 and 4 as a bone screw), a saddle 16, a seat 20, and a seat fastener 30.

Figure 4:
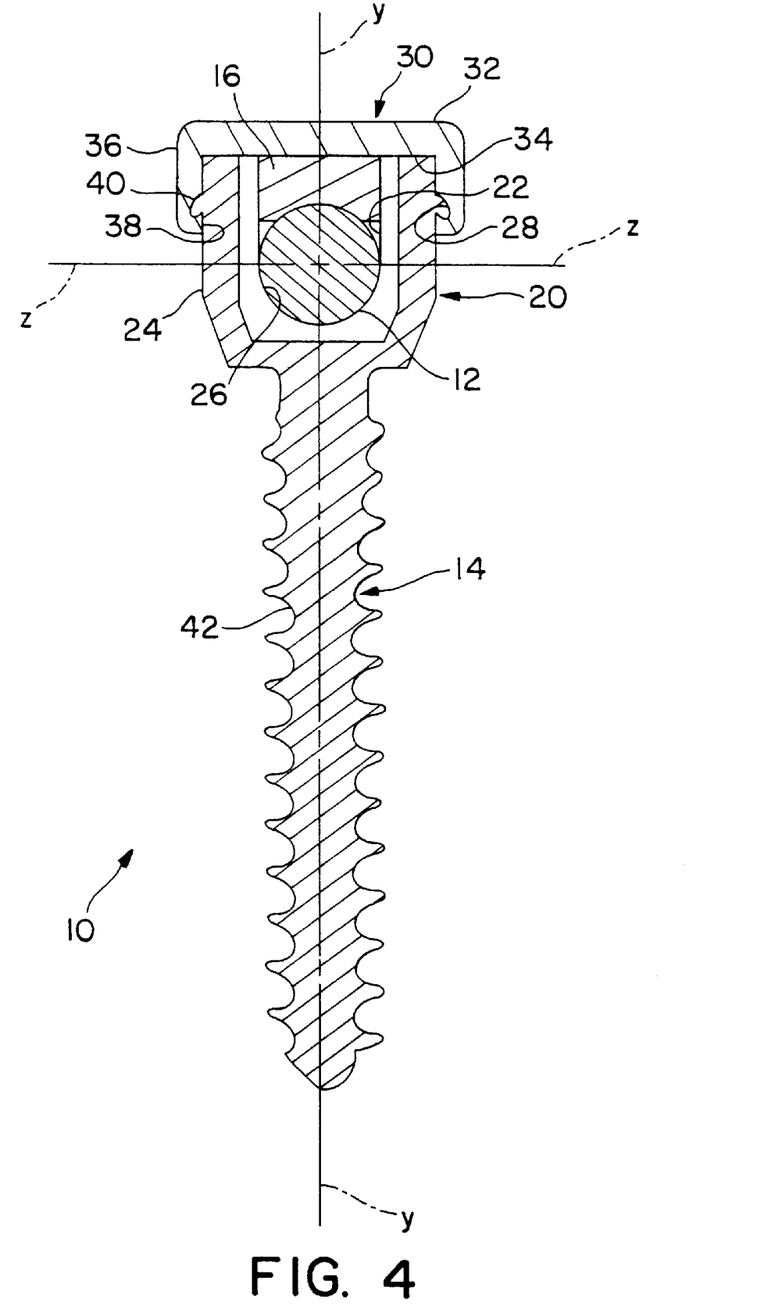
FIG. 4 is a cross-section of the spinal fixation device of FIG. 3 taken at the Y/Z-plane of the device.

Seat 20 includes an outer seat surface 24, and an inner seat surface 22 which preferably forms a cross-sectional U-shape. Seat 20 also includes brace canal 26, forming the base of the U-shape, which extends in a direction substantially perpendicular to the Y-axis and the Z-axis of fixation device 10 through seat 20 as illustrated in FIGS. 1, 2, and 4.

The spinal fixation assembly further includes a seat fastener 30 having a top 32, a bottom 34, an outer side surface 36, and an inner side surface 38. The seat fastener preferably includes chamfer or rounded edge(s) to reduce potentially tissue-irritating edges of the seat fastener which would be exterior relative to the bone, but possibly juxtaposed to a variety of soft tissues. The shape and size of outer side surface 36 and top 32 of seat fastener 30 are not critical, but optimum shape(s) and/or size(s) of outer side surface 36 and/or top 32 of seat fastener 30 will be obvious to those of ordinary skill in the art.

Additionally, FIGS. 1–4 illustrate seat 20 and seat fastener 30 having a relationship wherein the outer side surface of the seat fastener extends out further than does that of outer seat surface 24. However, in some embodiments, seat 20 and seat fastener 30 are designed and configured such that outer side surface 36 of seat fastener 30 is in substantial alignment with outer seat surface 24 of seat 20. In yet other embodiments, seat 20 and seat fastener 30 are designed and configured such that outer seat surface 24 of seat 20 extends out further than does that of outer side surface 36 of seat fastener 30.

FIGS. 1 and 2 illustrate two preferred embodiments of the connecting relationship between seat 20 and seat fastener 30. Referring to FIG. 1, seat fastener 30 connects to seat 20 via cooperative engagement between a locking channel 28A of seat 20 and a helical dove-tailed lip 40A of seat fastener 30. Similarly, referring to FIG. 2, seat fastener 30 connects to seat 20 via cooperative engagement between a locking channel 28B of seat fastener 30 and a helical dove-tailed lip 40B of seat 20. In most embodiments, locking channel 28A is generally machined into seat 20, or, in the alternative, locking channel 28B is generally machined into seat fastener 30.

In preferred embodiments, the helical dove-tailed lip forms a mating relationship with the locking channel in order to indirectly apply a compressive force on elongate brace member 12 through the use of saddle 16, functioning as a force transfer intermediary. Brace member 12 is compressively loaded into a fixing cooperation between inner seat surface 22 and saddle 16 by compression resulting from tightening seat fastener 30 to seat 20. In addition, as is shown in FIGS. 1 and 2, saddle 16 preferably includes a contoured bottom surface which is complimentary to the elongate surface of brace member 12 to provide and/or enhance a fixing/locking interface between saddle 16 and elongate brace member 12 when seat fastener 30 is affixed to seat 20.

Saddle 16 preferably has a Y-axis thickness slightly greater than the distance between seat fastener 30, in its tightened position, and a respective portion of elongate brace member 12 associated with the saddle, such that saddle 16 can function to relay the pressure created between seat 20 and seat fastener 30, due to the novel external combination of the locking channel and helical dove-tailed lip, to elongate brace member 12, thereby isolating such brace member.

Saddle 16 can comprise any material which can function to stabilize the elongate brace member 12 after seat fastener 30 is tightened about seat 20. Additionally, at least the surface of saddle 16 which is in direct contact with elongate brace member 12 can be roughed to enhance the stabilization ability of saddle 16 when the seat fastener is in its tightened position with relationship to the seat.

In some embodiments, the saddle and the seat fastener can be combined as one unit wherein the saddle is attached to the seat fastener e.g. rotationally attached via a swivel, or the like, to allow the seat fastener to lockingly engage the seat while keeping the saddle in an appropriate stabilizing position with respect to the elongate brace member. helical dove-tailed lip of the device. In preferred embodiments, a helical dove-tail of the device tapers about 0.02 inch to about 0.07 inch over approximately a 180 degree arc, more preferably about 0.03 inch to about 0.06 inch over approximately a 180 degree arc, even more preferably about 0.04 inch to about 0.05 inch over approximately a 180 degree arc, and most preferably about 0.043 inch to about 0.045 inch over approximately a 180 degree arc. Therefore, upon appropriately engaging the seat fastener atop the seat, the seat fastener locks with an approximately 90 degree turn to create a compressional immobilizing force between the seat, the elongate brace device, the saddle, and the seat fastener.

The resulting connection is superior to conventional devices and methods in that the locking engagement between the locking channel and the helical dove-tailed lip of the device provide easy installation and less chance for device failure due to expansive lateral pressure using caps which are disposed interior to the seat.

Seat fastener/seat assembly of the invention also provides greater resistance to torsional slip than comparable set screws, and such assembly preferably installs with a torque level of about 70 in-lb. to about 90 in-lb. The torque required to attach a seat fastener to a respective seat may vary, and is dependent upon the taper of both the locking channel and the helical dove-tailed lip, and the thickness of the saddle, as well as, amongst other factors, whether the respective surfaces are anodized.

The helical dove-tailed lip generally comprises a lower surface, an upper surface, and a lateral surface. Either the upper surface or the lower surface, and the lateral surface meet to form a dove-tailed lip which can have a variety of configurations as long as such lip functions to hold the corresponding seat or seat fastener, of which it is a component, to the companion seat or seat fastener. The locking channel generally has a floor, a side wall, and a ceiling. One or more of the floor, side wall, and ceiling is shaped, e.g. sloped or angled, to correspond to the shape of the helical dove-tailed lip.

In the alternative, the lock-notch and lock-groove can be arranged for axial movement of the lock-notch into the lock-groove whereby the notch and groove are disposed on respective surfaces of the seat fastener and the seat which face inwardly and outwardly of the seat.

In some embodiments, one or more of the floor, side wall, and ceiling of the locking channel has a lock-groove which comprises a recess of about 0.001 mm to about 0.01 mm and preferably about 0.003 mm to about 0.007 mm, and is generally disposed at or near a respective portion of the channel closest in proximity to the bottom surface of the seat fastener when the seat and seat fastener are affixed to one another. Correspondingly, in such embodiments, the respective complimentary surface(s) of the helical dove-tailed lip has a lock-notch which comprises a protrusion compatible in size, shape and orientation with the aforementioned lock-groove such that, as the seat fastener is torqued atop the seat, the lock-notch of the helical dove-tailed lip approaches the lock-groove of the locking channel until such lock-notch engages such lock-groove, thus providing additional securement means between the seat and seat fastener. Other embodiments are also comprehended wherein the lock-notch is disposed on the locking channel, and the lock-groove is disposed in the helical dove-tailed lip.

In some embodiments, the seat and/or seat fastener include visual alignment indicators to ensure that the installer twists no more or no less than the about 90 degrees required for a sufficient locking engagement. Such visual alignment indicators are preferably etched or laser-marked onto the respective seat and/or, seat fastener.

Figure 3:
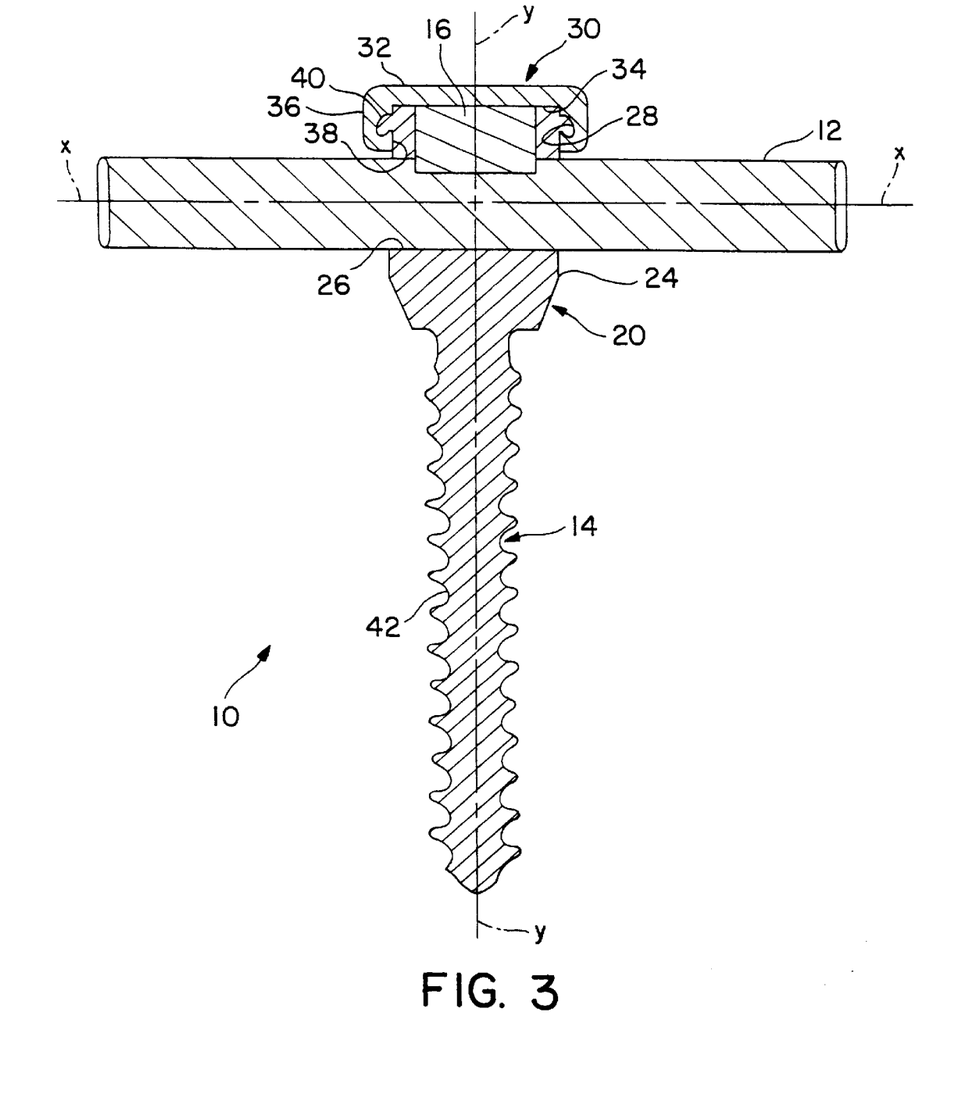
FIG. 3 is a cross-section of a spinal fixation device of the invention as in FIG. 2 taken at the X/Y-plane of the device.

Referring to FIGS. 3 and 4, spinal fixation device 10 includes an attachment component 14 which functions to affix the spinal fixation device to the respective bone. Attachment component 14, as shown in FIGS. 3 and 4, can comprise threaded portion 42, i.e. a screw shaft, which is driven into the respective bone.

In some embodiments, the attachment component can be a headed screw which is inserted through the seat and into the bone, thus making the seat and the attachment component two separate elements of the spinal fixation device. In other embodiments, the attachment component can be a headed screw which has a modified ball joint on the bottom surface of the screw head and which is inserted through an internal surface of the seat, which is designed and configured to conform to the rounded shape of the head, and into the bone, thus allowing for varying degrees of angular adjustment of the seat about the screw head after the screw has been driven into the bone.

Figure 5:
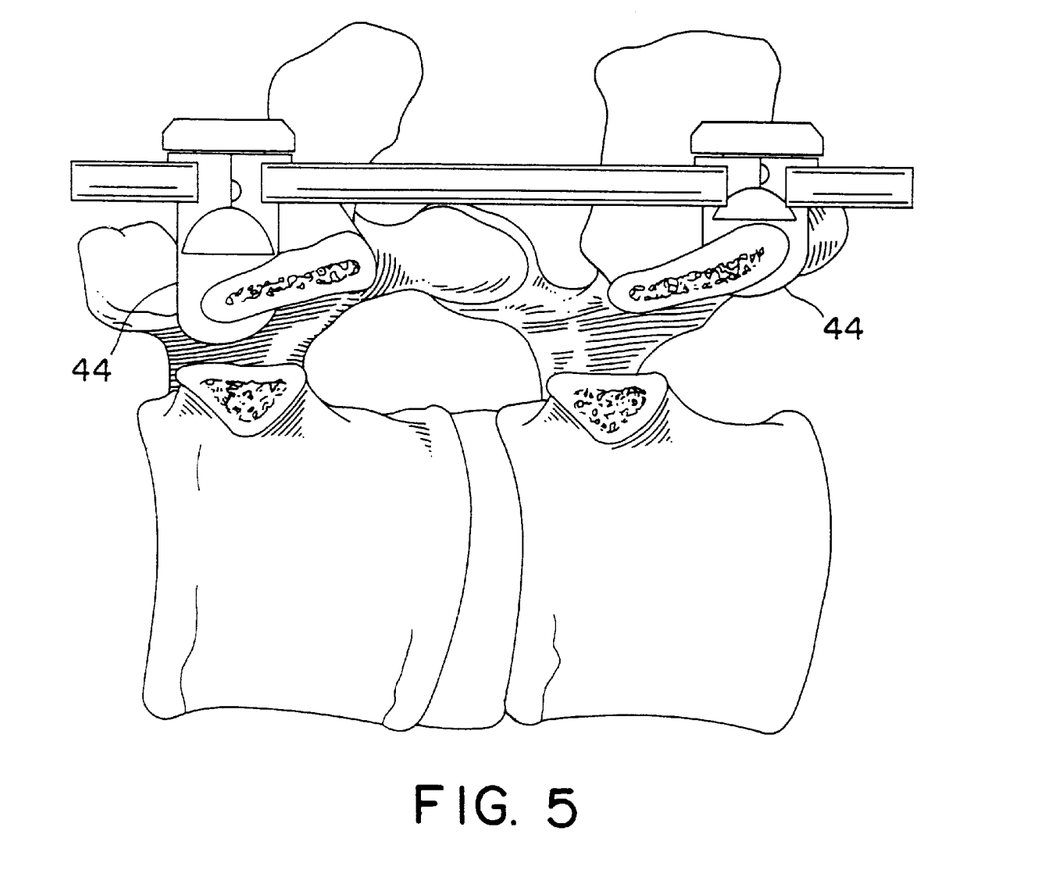
FIG. 5 is a side pictorial view of a conventional spinal fixation apparatus illustrating laminar hooks.

In an alternative, the attachment component is a type of hook such as e.g. a lamina hook, which generally is affixed/wrapped-around the flattened part of either lateral side of the arch of a respective vertebrae, or e.g. a pedicle hook, which generally is affixed/wrapped-around the bony process of a respective vertebrae that projects dorsally from the body of a vertebra connecting with the lamina on each side. Vertebral hooks, such as laminar hooks and pedicle hooks, being used as attachment components is well known in the art. A conventional vertebral support device, including laminar hooks 44, is illustrated in FIG. 5. Other attachment components for affixing bone fixation devices to desired bones will be obvious to those of ordinary skill in the art; thus such other attachment components are also contemplated as comprising attachment component 14.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A spinal fixation device for use with an elongate brace member, said spinal fixation device comprising;
   (a) a bone attachment component for securing said spinal support device to desired bone structure;
   (b) a seat, said seat comprising an inner seat surface and an outer seat surface, said seat having a brace canal along the inner seat surface for positioning of such brace member, said outer seat surface having a locking channel;

(c) a seat fastener having a top, a bottom, an outer side surface, and an inner side surface, said inner side surface including a lip; and (d) a saddle suitable for disposition between such brace member and said seat fastener, said locking channel of said seat being designed and configured to form a cooperative engagement with said lip of said seat fastener wherein, upon engaging of said seat fastener atop said seat, said seat fastener locks with an approximate 90 degree turn to create a compressional immobilizing force between said seat, said seat fastener, said saddle, and such elongate brace member received in said brace canal.

2. A spinal fixation device as in claim 1 wherein said bone attachment component comprises a threaded screw portion, a lamina hook, or a pedicle hook.

3. A spinal fixation device as in claim 1 wherein said cooperative engagement between said lip of said seat fastener and said locking channel of said seat is a high friction interface.

4. A spinal fixation device as in claim 1, said lip of said seat fastener further comprising a lock-notch, and said locking channel of said seat further comprising a complimentary lock-groove which comprises a recess of about 0.001 mm to about 0.01 mm, said lock-notch comprising a protrusion compatible in size, shape, and orientation with said lock-groove such that, upon sufficient rotation of said seat fastener, the lock-notch interfaces with the lock-groove, thereby further securing the cooperative engagement between said lip of said seat fastener and said locking channel of said seat.

5. A spinal fixation device as in claim 1, said lip of said seat fastener further comprising a lock-groove which comprises a recess of about 0.001 mm to about 0.01 mm, and said locking channel of said seat further comprising a complimentary lock-notch which comprises a protrusion compatible in size, shape, and orientation with said lock-groove such that, upon sufficient rotation of said seat fastener, the lock-notch interfaces with the lock-groove, thereby further securing the cooperative engagement between said lip of said seat fastener and said locking channel of said seat.

6. A spinal fixation device as in claim 1 wherein the spinal fixation device is anodized.

7. A spinal fixation device as in claim 1 wherein said spinal fixation device is made of titanium.

8. A spinal fixation device as in claim 1 wherein said lip tapers at a rate of about 0.04 inch to about 0.05 inch inch over a 180 degree arc.

9. A spinal fixation device as in claim 1 wherein at least one of said seat and said seat fastener have visual alignment indicators which come into desired alignment upon rotating said seat fastener approximately 90 degrees.

10. A spinal fixation device as in claim 1 wherein said saddle is a separate and distinct element of said spinal fixation device.

11. A spinal fixation device as in claim 10 wherein said saddle is rotationally attached to said seat fastener.

12. A spinal fixation device for use with an elongate brace member, said spinal fixation device comprising;

(a) a bone attachment component for securing said spinal support device to desired bone structure;

(b) a seat, said seat comprising an inner seat surface and an outer seat surface, said seat having a brace canal along the inner seat surface for positioning of such brace member, said outer seat surface having a lip;

(c) a seat fastener having a top, a bottom, an outer side surface, and an inner side surface, said inner side surface including a locking channel; and (d) a saddle suitable for disposition between such brace member and said seat fastener, said locking channel of said seat fastener being designed and configured to form a cooperative engagement with said lip of said seat, wherein, upon engaging of said seat fastener atop said seat, said seat fastener locks with an approximate 90 degree turn to create a compressional immobilizing force between said seat, said seat fastener, said saddle, and such elongate brace member received in said brace canal.

13. A spinal fixation device as in claim 12 wherein said bone attachment component comprises a threaded screw portion, a lamina hook or a pedicle hook.

14. A spinal fixation device as in claim 12 wherein said cooperative engagement between said lip of said seat and said locking channel of said seat fastener is a high friction interface.

15. A spinal fixation device as in claim 12, said lip of said seat further comprising a lock-notch, and said locking channel of said seat fastener further comprising a complimentary lock-groove which comprises a recess of about 0.001 mm to about 0.01 mm, said lock notch comprising a protrusion compatible in size, shape, and orientation with said lock-groove such that, upon sufficient rotation of said seat fastener, the lock-notch interfaces with the lock-groove, thereby further securing the cooperative engagement between said lip of said seat and said locking channel of said seat fastener.

16. A spinal fixation device as in claim 12, said lip of said seat further comprising a lock-groove which comprises a recess of about 0.001 mm to about 0.01 mm, and said locking channel of said seat fastener further comprising a complimentary lock-notch which comprises a protrusion compatible is size, shape, and orientation with said lock-groove such that, upon sufficient rotation of said seat fastener, the lock-notch interfaces with the lock-groove, thereby further securing the cooperative engagement between said lip of said seat and said locking channel of said seat fastener.

17. A spinal fixation device as in claim 12 wherein the spinal fixation device is anodized.

18. A spinal fixation device as in claim 12 wherein said spinal fixation device is made of titanium.

19. A spinal fixation device as in claim 12 wherein said lip tapers at a rate of about 0.04 inch to about 0.05 inch inch over a 180 degree arc.

20. A spinal fixation device as in claim 12 wherein at least one of said seat and said seat fastener have visual alignment indicators which come into desired alignment upon rotating said seat fastener approximately 90 degrees.

21. A spinal fixation device as in claim 12 wherein said saddle is a separate and distinct element of said spinal fixation device.

22. A spinal fixation device as in claim 21 said saddle is rotationally attached to said seat fastener.

23. A spinal fixation device for use with an elongate brace member, said spinal fixation device comprising;

(a) a bone attachment component for securing said spinal support device to desired bone structure;

(b) a seat, said seat comprising an inner seat surface and an outer seat surface, said seat having a brace canal along the inner seat surface for positioning of such brace member; and (c) a seat fastener having a top, a bottom, an outer side surface, and an inner side surface, said seat and said seat fastener collectively comprising rotationally engaging joinder elements effective, upon engaging of said seat fastener atop said seat, said seat fastener locks with an approximate 90 degree turn to create a compressional immobilizing force between said seat, said seat fastener, and such elongate brace member received in said brace canal.

24. A spinal fixation device as in claim 23 wherein said seat fastener bears against a saddle which bears on such brace member thus to urge such brace member into secure engagement with said brace canal of said seat.

25. A spinal fixation device as in claim 23 wherein at least one of said seat and said seat fastener has a visual alignment indicator which comes into desired alignment upon rotating said seat fastener approximately 90 degrees.

26. A spinal fixation device as in claim 23, further comprising a saddle rotationally attached to said seat fastener, the rotation of said seat fastener urging said saddle against such brace member thus to bring such brace member into secure engagement with said brace canal of said seat.

* * * * *